United States Patent [19]

Smith et al.

[11] Patent Number: 5,409,934
[45] Date of Patent: Apr. 25, 1995

[54] XANTHINE DERIVATIVES

[76] Inventors: David G. Smith; Derek R. Buckle; Ashley E. Fenwick, all of SmithKline Beecham Pharmaceuticals, Great Burgh, Yew Tree Bottom Road, Epson, Surrey, England, KT18 5XQ

[21] Appl. No.: 78,152
[22] PCT Filed: Dec. 19, 1991
[86] PCT No.: PCT/GB91/02286
  § 371 Date: Jul. 7, 1993
  § 102(e) Date: Jul. 7, 1993
[87] PCT Pub. No.: WO/9211260
  PCT Pub. Date: Jul. 9, 1992

[30] Foreign Application Priority Data

Dec. 21, 1990 [GB] United Kingdom ............... 9027752
Dec. 21, 1990 [GB] United Kingdom ............... 9027899

[51] Int. Cl.$^6$ ............... C07D 473/06; C07D 473/10; A61K 31/52
[52] U.S. Cl. ............... 514/263; 514/826; 544/267; 544/268; 544/272
[58] Field of Search ............... 544/267, 268, 272; 514/263

[56] References Cited

U.S. PATENT DOCUMENTS 3,900,474  8/1975  Ginger ............... 260/256

FOREIGN PATENT DOCUMENTS 0400356  12/1990  European Pat. Off.

OTHER PUBLICATIONS

Chemical Abstracts vol. 5467676 6, 10 Apr. 1960, Hiromu Morishita: 'Xanthine-type sulfonamide derivatives.'
Chemical Abstracts, vol. 85, No. 25, 20 Dec. 1976, abstract No. 187194, Acatrinei G.
Journal of Pharmaceutical Sciences vol. 67, No. 8, 8 Aug. 1978, Washington DC pp. 1045–1050; Nicholas Bodor E. A.: 'Controlled Delivery of Theophylline.'

Primary Examiner—Mark L. Berch
Attorney, Agent, or Firm—James Kanagy; Stuart Suter; Edward Lentz

[57] ABSTRACT

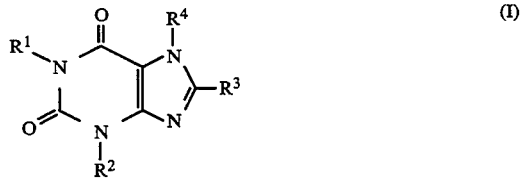

(I)

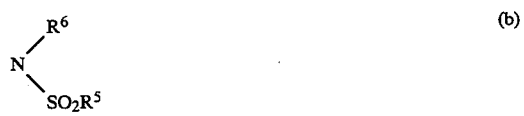

(b)

A compound of formula (I) or, if appropriate, a pharmaceutically acceptable salt thereof, wherein $R^1$ and $R^2$ each independently represent an alkyl group or a moiety of formula (a): —$(CH_2)_m$—A, wherein m represents zero or an integer 1, 2 or 3 and A represents a substituted or unsubstituted cyclic hydrocarbon radical; $R^3$ represents hydrogen, $NO_2$ or a halogen atom, an alkoxy group or a group of formula $NR^sR^t$ wherein $R^s$ and $R^t$ each independently represent hydrogen or alkyl or $R^s$ and $R^t$ together with the nitrogen to which they are attached form a phthalimido group, the phthalimido group being substituted or unsubstituted in the phenylene moiety or $R^3$ represents a moiety of formula (b), wherein $R^5$ represents substituted or unsubstituted alkyl or a substituted or unsubstituted aryl group; and $R^6$ represents hydrogen or a group $SO_2R^7$ wherein $R^7$ represents substituted or unsubstituted alkyl, a substituted or unsubstituted aryl group; $R^4$ represents $SO_2R^8$, wherein $R^8$ represents substituted or unsubstituted alkyl or a substituted or unsubstituted aryl group, or, when $R^3$ represents a moiety of the above-defined formula (b), then $R^4$ represents hydrogen or a substituted or unsubstituted alkyl group or a benzyl group substituted or unsubstituted in the phenyl ring a process for preparing such a compound, a composition comprising such a compound and the use of such a compound and composition in medicine.

9 Claims, No Drawings

XANTHINE DERIVATIVES

The present invention relates to certain novel compounds having pharmacological activity, to a process for the preparation of such compounds, to pharmaceutical compositions containing such compounds and to the use of such compounds and compositions in medicine.

EP 0389282 discloses a series of 8-substituted xanthines useful in the treatment of disorders of the respiratory tract.

It has been discovered that a novel series of sulphonated xanthines have particularly good activity as phosphodiesterase inhibitors.

These compounds are therefore potentially useful as bronchodilators in the treatment of disorders of the respirator tract, such as reversible airways obstruction and asthma.

These compounds are also indicated to be good inhibitors of induced blood eosinophilia and they are therefore potentially useful in the treatment and/or prophylaxis of disorders associated with increased numbers of eosinophils, such as asthma, and allergic disorders associated with atopy, such as urticaria, eczema and rhinitis.

These compounds may also have a protective effect against the consequences of cerebral metabolic inhibition. The said compound improve data aquisition or retrieval following transient forebrain ischaemia and are therefore useful in the treatment of cerebral vascular and neuronal degenerative disorders associated with learning, memory and cognitive dysfunctions including cerebral senility, multi-infarct dementia, senile dementia of the Alzheimer type, age associated memory impairment and certain disorders associated with Parkinson's disease.

These compounds are also indicated to have neuroprotectant activity. They are therefore useful in the prophylaxis of disorders associated with neuronal degeneration resulting from ischaemic events, including cerebral ischaemia due to cardiac arrest, stroke and also after cerebral ischaemic events such as those resulting from surgery and/or during childbirth. In addition treatment with the compound is indicated to be of benefit for the treatment of functional disorders resulting from disturbed brain function following ischaemia.

These compounds are also active in increasing the oxygen tension in ischaemic skeletal muscle. This property results in an increase in the nutritional blood flow through ischaemic skeletal muscle which in turn indicates that the compounds of the invention are of potential use as agents for the treatment of peripheral vascular disease such as intermittent claudication.

As these compounds elevate cyclic AMP levels they are also of potential use in the treatment of proliferative skin disease in human or non-human mammals.

In addition these compounds may also have potential as inhibitors of the production of tumour necrosis factor (TNF) and hence have potential for the treatment of human immunodeficiency virus (HIV), acute immune deficiency syndrome (AIDS), rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, pulmonary inflammatory disease, bone resorption diseases, reperfusion injury, graft vs. host reaction, fever and myalgias due to infection, such as influenza, cachexia secondary to infection or malignancy, cachexia secondary to AIDS, keloid formation, scar tissue formation, Crohn's disease, ulcerative colitis, or pyresis.

Accordingly, the invention also provides a compound of formula (I):

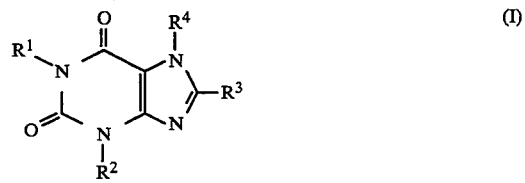

or if appropriate, a pharmaceutically acceptable salt thereof, wherein $R^1$ and $R^2$ each independently represent an alkyl group or a moiety of formula (a):

$$-(CH_2)_m-A \qquad (a)$$

wherein m represents zero or an integer 1, 2 or 3 and A represents a substituted or unsubstituted cyclic hydrocarbon radical; $R^3$ represents hydrogen, $NO_2$ or a halogen atom, an alkoxy group or a group of formula $NR^sR^t$ wherein $R^s$ and $R^t$ each independently represent hydrogen or alkyl or $R^s$ and $R^t$ together with the nitrogen to which they are attached form a phthalimido group, the phthalimido group being substituted or unsubstituted in the phenylene moiety or $R^3$ represents a moiety of formula (b):

wherein $R^5$ represents substituted or unsubstituted alkyl or a substituted or unsubstituted aryl group and $R^6$ represents hydrogen or a group $SO_2R_7$ wherein $R_7$ represents substituted or unsubstituted alkyl, or a substituted or unsubstituted aryl group; $R^4$ represents $SO_2R_8$, wherein $R^8$ represents substituted or unsubstituted alkyl or a substituted or unsubstituted aryl group, or, providing $R^3$ represents a moiety of the abovedefined formula (b), then $R^4$ may also represent hydrogen, a substituted or unsubstituted alkyl group or a benzyl group substituted or unsubstituted in the phenyl ring.

Suitably, one of $R^1$ or $R^2$ may represent alkyl and the other a moiety of formula (a).

Preferably, $R^1$ and $R^2$ both represent a moiety of formula (a).

Suitably, A represents a substituted or unsubstituted alicyclic hydrocarbon radical.

Favourably, A represents a substituted or unsubstituted $C_{3-8}$ cycloalkyl group, especially a $C_{3-6}$ cycloalkyl group.

In particular, A represents a substituted or, preferably, unsubstituted cyclopropyl, cyclobutyl, cyclopentyl or cyclohexyl group.

Suitably, A is unsubstituted.

Favourably, A represents a cyclopropyl group or a cyclobutyl group.

Preferably, A represents a cyclopropyl group.

Suitably, $R^3$ represents hydrogen, a halogen atom, a group of the abovedefined formula $NR^sR^t$, or a moiety of the abovedefined formula (b), especially a group of formula $NR^sR^t$ and a group of formula (b).

Preferably, $R^3$ represents a group of formula $NR^sR^t$.

Suitably, $R^s$ and $R^t$ each independently represent hydrogen or alkyl.

Preferably, $R^s$ and $R^t$ each represent hydrogen.

When $R^3$ is a moiety of formula (b), $R^6$ may represent hydrogen or a group $SO_2R^7$, but it is preferred if R6 is hydrogen.

Examples of $R^3$ are $NH_2$, Cl or a phthalimido group: A further example is hydrogen.

Suitable substituted or unsubstituted aryl groups include substituted or unsubstituted phenyl groups.

Favoured substituents for any aryl group include up to five groups, but preferably up to 3 groups, selected from halogen, alkyl, alkoxy, haloalkyl, amino, monoalkylamino, bisalkylamino, monoalkylcarbonylamino, bisalkylcarbonylamino, hydroxy, nitrile, nitro and carboxy; and also alkoxycarbonyl.

Preferred substituents include halogen, alkyl, alkoxy, haloalkyl, nitro and alkoxycarbonyl, especially alkoxy.

Examples of substituent for any aryl group include chlorine, bromine, methyl, i-propyl, trifiuoromethyl, vitro and methoxycarbonyl.

Preferably, $R^5$ represents a substituted aryl group.

Preferably, $R^7$ represents a substituted aryl group.

Preferably, $R^8$ represents a substituted aryl group.

Particular, examples of substituents for any aryl group represented by $R^5$, include methoxy, especially 4-methoxy: Also included is nitro, especially 4-nitro.

Particular examples of substituents for any aryl group represented by $R^7$, include methoxy, especially 4-methoxy: Also included is nitro, especially 4-nitro.

Particular examples of substituents for any aryl group represented by $R^8$, include bromo, methoxy and vitro: Also included are methyl, chloro, trifluoromethyl and methoxycarbonyl.

Particular examples of $R^8$ aryl groups include phenyl, 4-methoxyphenyl, 3,4-dimethoxyphenyl, 2,5-dimethoxyphenyl, (2-methoxy,5-bromo)phenyl and 4-nitrophenyl. Also included are 3- or 4-trifiuoromethylphenyl, (3,5-di-trifiuoromethyl)phenyl, 4-chlorophenyl, 4-methylphenyl, 3,4,5-trimethoxyphenyl and 2-methoxycarbonylphenyl.

One preferred value for $R^8$ is 4-methoxyphenyl.

In one aspect when $R^3$ is a moiety (b) $R^4$ represents hydrogen.

When $R^3$ is (b), $R^4$ may also represent substituted or unsubstituted alkyl or benzyl substituted or unsubstituted in the phenyl ring.

In a further aspect, $R^4$ represents $SO_2R^8$.

When $R^4$ represents alkyl it is suitably methyl.

When $R^4$ represents substituted benzyl, suitable substituents include alkoxy groups, especially methoxy groups, particular examples include 4-methoxyphenylmethyl and 3,4,5-trimethoxyphenylmethyl.

Suitably, $R^6$ represents hydrogen.

Favourably, m represents 1.

In one aspect the invention provides a compound of formula (I) or, if appropriate, a pharmaceutically acceptable salt thereof, wherein $R^1$ and $R^2$ each independently represent an alkyl group or a moiety of formula (a):

$$-(CH_2)_m-A \qquad (a)$$

wherein m represents zero or an integer 1, 2 or 3 and A represents a substituted or unsubstituted cyclic hydrocarbon radical; $R^3$ represents $NO_2$ or a halogen atom, an alkoxy group or a group of formula $NR^sR^t$ wherein $R^s$ and $R^t$ each independently represent hydrogen or alkyl or $R^s$ and $R^t$ together with the nitrogen to which they are attached form a phthalimido group, the phthalimido group being substituted or unsubstituted in the phenylene moiety; and $R^4$ represents a substituted or unsubstituted aryl group.

In a further aspect the invention provides a compound of formula (I) or, if appropriate, a pharmaceutically acceptable salt thereof, wherein $R^1$ and $R^2$ each independently represents an alkyl group or a moiety of formula (a):

$$-(CH_2)_m-A \qquad (a)$$

wherein m represents zero or an integer 1, 2 or 3 and A represents a substituted or unsubstituted cyclic hydrocarbon;

$R^5$ represents a substituted or unsubstituted aryl group; and $R^6$ represents hydrogen or a group $SO_2R^7$ wherein $R^7$ represents a substituted or unsubstituted aryl group; and $R^4$ represents an alkyl group or a benzyl group substituted or unsubstituted in the phenyl ring.

Suitable pharmaceutically acceptable salts are pharmaceutically acceptable base salts and pharmaceutically acceptable acid addition salts. Suitable pharmaceutically acceptable base salts of the compounds of formula (I) include base salts including metal salts, such as alkali metal salts for example sodium salts, or organic amine salts such as that provided with ethylenediamine.

Suitable acid addition salts of the compounds of formula (I) are the acid addition salts including pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methanesulphonate, a-keto glutarate, a-glycerophosphate and glucose-1-phosphate. Preferably the acid addition salt is a hydrochloride salt.

The present invention also encompasses a solvate, such as a hydrate, of a compound of formula (I) or a pharmaceutically acceptable salt thereof.

The pharmaceutically acceptable salts of the compounds of formula (I) are prepared using conventional procedures.

The pharmaceutically acceptable solvates of the compounds of formula (I) or the pharmaceutically acceptable solvates thereof are prepared using conventional procedures.

When used herein the term 'cyclic hydrocarbon radical' includes single ring and fused ring, alicyclic hydrocarbons comprising up to 8 carbon atoms in each ring, suitably up to 6 carbon atoms, for example 3, 4, 5 or 6 carbon atoms.

Suitable optional substituents for any cyclic hydrocarbon radical includes a $C_{1-6}$ alkyl group or a halogen atom.

When used herein the term 'alkyl' whether used alone or when used as part of another group (for example as in an alkylcarbonyl group) includes straight and branched chain alkyl groups, containing from 1 to 12 carbon atoms, suitably 1 to 6 carbon atoms, for example methyl, ethyl, propyl or butyl.

Suitable substituents for any alkyl group include those mentioned in regard to aryl groups.

When used herein, unless otherwise indicated the term 'aryl' includes phenyl and naphthyl optionally substituted with up to five groups, preferably up to three groups, selected from halogen, alkyl, phenyl, alkoxy, haloalkyl, hydroxy, amino, monoalkylamino, bisalkylamino, monoalkylcarbonylamino, bisalkylcarbonylamino, nitro, nitrile, carboxy, alkoxycarbonyl, alkoxycarbonylalkyl, alkylcarbonyloxy and alkylcarbonyl groups.

When used herein the expression 'proliferative skin diseases' means benign and malignant proliferative skin diseases which are characterized by accelerated cell division in the epidermis, dermis or appendages thereto, associated with incomplete tissue differentiation. Such diseases include: psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

The compounds of formula (I) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

The invention further provides a process for the preparation of a compound of formula (I), which process comprises:

a) for compounds of formula (I) wherein $R^4$ is $-SO_2R^8$ and $R^3$ represents hydrogen, $NO_2$, halogen, an alkoxy group or a group of the abovedefined formula $NR^sR^t$, by reacting an activated form of a compound of formula (II):

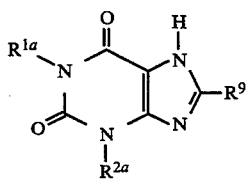

(II)

wherein $R^{1a}$ represents $R^1$, as defined in relation to formula (I), or a group convertible to $R^1$ and $R^{2a}$ represents $R^2$, as defined in relation to formula (I), or a group convertible thereto and $R^9$ is hydrogen, $NO_2$, halogen, alkoxy or a group of the abovedefined formula $NR^sR^t$, or a group convertible thereto, with a compound of formula (III):

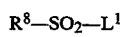  (III)

R$^8$—SO$_2$—L$^1$ wherein $R^8$ is as defined in relation to formula (I) and $L^1$ represents a leaving group;

b) for compounds of formula (I) wherein $R^4$ represents hydrogen, an alkyl group, a benzyl group substituted or unsubstituted in the phenyl ring or a group $SO_2R^8$ wherein $R^8$ is equal to $R^5$ and $R^3$ is a moiety of the abovedefined formula (b) wherein $R^6$ is hydrogen or a group $R^5SO_2$, by reacting a compound of formula (IV):

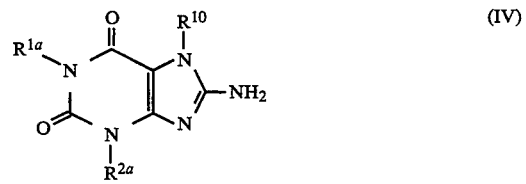

wherein $R^{1a}$ and $R^{2a}$ are as defined in relation to formula (II) and $R^{10}$ represents hydrogen, an alkyl group or a benzyl group substituted or unsubstituted in the phenyl ring, or a group convertible thereto, with an appropriate amount of a compound of formula (V) in the presence of an appropriate amount of a base:

$R^{11}$—SO$_2$—L$^2$     (V)

wherein $R^{11}$ is $R^5$ for effecting sulphonation of the NH$_2$ group or $R^{11}$ is $R^8$ for effecting sulphonation of the 7-N atom, as necessitated by the required compound of formula (I) and $L^2$ represents a leaving group; or c) for compounds of formula (I) wherein $R^4$ represents hydrogen, an alkyl group or a benzyl group substituted or unsubstituted in the phenyl ring or a group $SO_2R^8$ and $R^3$ represents a moiety of the abovementioned formula (b) wherein $R^6$ represents $R^7SO_2$—, and wherein $R^5$, $R^7$ and $R^8$ are different one from the other, by reacting an activated form of a compound of formula (VI):

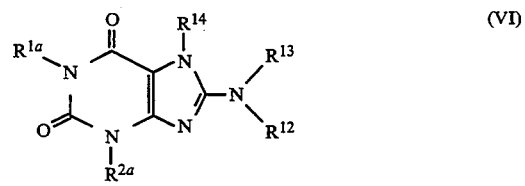

wherein $R^{1a}$ and $R^{2a}$ are as defined in relation to formula (IV), $R^{12}$ is hydrogen, a protecting group or $R^5SO_2$, $R^{13}$ is hydrogen, a protecting group or $R^7SO_2$ and $R^{14}$ is hydrogen, a protecting group or $R^8SO_2$, providing that one or two of $R^{12}$, $R^{13}$ and $R^{14}$ represents hydrogen, with a compound of formula (VII):

$R^{15}SO_2L^3$     (VII)

wherein $R^{15}$ is $R^5$, $R^7$ or $R^8$ as appropriate for the required compound of formula (I), and $L^3$ represents a leaving group, and thereafter as appropriate for the required compound of formula (I) reacting the product with a different compound of formula (VII); and thereafter, if required carrying out one or more of the following optional steps:
 (i) converting any group $R^{1a}$ to $R^1$ and/or $R^{2a}$ to $R^2$;
 (ii) converting a compound of formula (I) into another compound of formula (I);
 (iii) converting a compound of formula (I) into a pharmaceutically acceptable salt thereof and]or a pharmaceutically acceptable solvate thereof.

Suitable leaving groups $L^1$, $L^2$ and $L^3$ include halo, for example a bromine or chlorine atom.

The reaction between compounds of formulae (II) and (III), (IV) and (V) and (VI) and (VII) may be carried out in an aprotic solvent, such as dimethylformamide, tetrahydrofuran or dimethoxyethane, at any temperature providing a suitable rate of formation of the required product, suitably an elevated temperature, for example in the range of from 30° C. to 100° C. and conveniently at 80° C.

A suitable activated form of a compound of formula (II) is a salted form, in particular an alkali metal salted form, for example a sodium or potassium salted form.

The activated form of a compound of formula (II) is prepared by the appropriate conventional procedure, for example a salted form may conveniently be prepared by treating the compound of formula (II) with a base. Suitable bases are organic bases such as amine bases, for example triethylamine, or, preferably, alkali metal bases, for example an alkali metal alkoxide such as potassium 1-butoxide or hydrides such as sodium hydride. Generally, the activated form of the compound of formula (II) is prepared in-situ in the same solvent as that used for reacting compounds of formula (II) and (III), at a temperature in the range of from 0° to 100° C., conveniently at ambient temperature.

In reaction a), when $R^9$ is a group convertible into hydrogen, $NO_2$, halogen, alkoxy or a group $NR^sR^t$, it is suitably an appropriate protecting group, which is removed and thereafter converted into the required group by conventional means. For example, when $R^3$ in the required compound of formula (I) is $NH_2$, it is preferred if $R^9$ is a protected —$NH_2$ group, using for example silyl protecting groups discussed hereinafter, the protecting group may then be removed to provide the appropriate compound of formula (I).

When $R^9$ in compound (II) represents $NH_2$, any mixture of products formed in the reaction may be separated using conventional methods such as chromatography to provide the required compound of formula (I).

Preferably, a small excess of base is used in the reaction between compounds (II) and (III), for example 1.1 to 1.3 moles of base per mole of the compound of formula (II). However, when $R^9$ in compound (II) represents —$NH_2$, it is preferred if an equivalent amount of base, preferably an alkali metal base, and compound (II) is used.

In the reaction between compounds of formulae (IV) and (V) a suitable base is an organic base such as an amine base, suitably with a pKa of 10 or less preferably about 5, for example triethylamine or pyridine, or the base may be an alkali metal base such as an alkali metal alkoxide, for example potassium t-butoxide.

The nature and amount of base and the amount of the compound of formula (V) can be important in determining the product produced in the reaction between compounds (IV) and (V). This is particularly important when $R^{10}$ in the compound of formula (IV) is hydrogen.

In regard to the nature of the base: generally, for the preparation of compounds of formula (I) wherein $R^6$ represents hydrogen, it is preferable if an an alkali metal base such as potassium t-butoxide is used. Alternatively, for the preparation of compounds of formula (I) wherein $R^6$ is $SO_2R^5$, it is preferable if an organic base is used, such as triethylamine or pyridine.

In reaction b), when $R^{10}$ in compound (IV) represents hydrogen and $R^4$ in the required compound of formula (I) is hydrogen, it is preferred if at least 2 moles of base, most preferably an alkali metal base, per mole of compound (IV) are used.

It will also be appreciated that in the reaction between compounds of formula (IV) and (V) the amount of compound (V) also dictates the nature of the final product. Generally, for the preparation of a compound of formula (I) wherein $R^4$ and $R^6$ each represent hydrogen, a substantially equimolar ratio of compounds of formulae (IV) and (V) (wherein $R^{11}$ is $R^5$) are used. For preparing compounds of formula (I) wherein $R^4$ is hydrogen and $R^6$ is $R^5SO_2$ it is usual to use a 1:2 ratio of the compounds of formula (IV) and (V) (wherein $R^{11}$ is $R^8$). For compounds of formula (I) wherein $R^4$ and $R^6$ each represent $R^{11}SO_2$ it is usual to use a 1:3 ratio of the compounds of formula (IV) and (V).

In a preferred form of reaction b), for preparing compounds of formula (I) wherein $R^4$ represents other than hydrogen:
a) compounds wherein $R^6$ is hydrogen are prepared by reacting a compound of formula (IV) with one equivalent of a compound of formula (V) in the presence of one equivalent of base;
b) compounds wherein $R^6$ is $R^5SO_2$ are prepared by reacting a compound of formula (IV) with two equivalents of a compound of formula (V) in the presence of two equivalents of base; and
c) compounds wherein $R^4$ is $R^8SO_2$ and $R^6$ is $R^5SO_2$ wherein $R^5$ is the same as $R^8$, are prepared by reacting a compound of formula (IV) with three equivalents of a compound of formula (V) in the presence of three equivalents of base.

In a further preferred form of reaction b) for preparing compounds of formula (I) wherein $R^4$ represents hydrogen:
a) compounds wherein $R^6$ is hydrogen are prepared by reacting a compound of formula (IV) with one equivalent of a compound of formula (V) in the presence of two equivalents of base; and
b) compounds wherein $R^6$ is $R^5SO_2$ are prepared by reacting a compound of formula (IV) with two equivalents of a compound of formula (V) in the presence of two equivalents of an organic base having a pKa of 10 or less, preferably about 5, for example pyridine.

A suitable activated form of a compound of formula (VI) is a salted form, in particular an alkali metal salted form, for example a potassium salted form.

The activated form of a compound of formula (VI) is prepared by the appropriate conventional procedure, for example that discussed above in relation to compounds of formula (II).

A compound of formula (VI) may be prepared from a compound of the abovedefined formula (IV) by reaction with a compound of the abovedefined formula (V) as described above, and thereafter protected as required.

The criteria dictating the type of base and the amount of base appropriate for the reaction between compounds, of formulae (VI) and (VII) are analogous to those described in relation to the reaction between compounds of formulae (IV) and (V).

Generally, one equivalent of the appropriate compound (VII) and one equivalent of the appropriate base are reacted with one equivalent of compound (VI).

When $R^{10}$ is a group convertible into hydrogen, an alkyl group or a benzyl group substituted or unsubstituted in the phenyl ring, it is suitably an appropriate protecting group, which may be removed and thereafter converted into the required group by conventional means.

For example, when $R^4$ in the required compound of formula (I) is hydrogen, then $R^{10}$ may be a protecting group such as an alkylsilyl group, which may be removed using methods described herein.

A compound of formula (II) may be prepared by reacting a compound of formula (VIII):

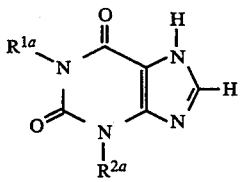

wherein $R^{1a}$ and $R^{2a}$ are as defined in relation to formula (II), with a reagent capable of substituting the C-8 hydrogen of the compound of formula (VIII) with a group $R^{9a}$ wherein $R^{9a}$ represents $R^9$, as defined above in relation to formula (II), or a group convertible thereto; and thereafter, if required carrying out one or more of the following optional steps:

(i) converting any group $R^{1a}$ to $R^1$ and/or $R^{2a}$ to $R^2$;
(ii) when $R^{9a}$ is not $R^9$, converting $R^{9a}$ to $R^9$.

For compounds of formula (II) wherein $R^9$ represents nitro, $R^{9a}$ preferably represents $R^9$ i.e. nitro.

For compounds of formula (II) wherein $R^{9a}$ represents other than nitro, $R^{9a}$ preferably represents a group convertible to $R^9$.

One preferred group $R^{9a}$ is a nitro group which may then if required be converted to another group $R^9$.

Suitable reagents for substituting the C-8 hydrogen of the compound of formula (VIII) with a group $R^{9a}$ are the appropriate conventional reagents.

The conditions of reaction for the substitution of the C-8 hydrogen of the compound of formula (VIII) will of course depend upon the particular reagent chosen, and in general the conditions used will be those which are conventional for the reagent used.

One particularly suitable reagent for preparing compounds having an 8-nitro substituent is a nitrating agent.

The nitration of compound (II) may be carried out using any suitable, conventional nitrating agent, for example a nitric acid/acetic acid mixture in an inert solvent, such as dichloromethane, at any temperature providing a convenient rate of formation of the required product, conveniently at ambient temperature.

In one convenient form of the abovementioned process the compound of formula (VIII) is reacted with a suitable nitrating agent to provide a compound of formula (II) wherein $R^9$ represents a nitro group and then converting the nitro group into a halogen atom or a group of the abovedefined formula $—NR^sR^t$, suitably via the halogen atom.

For example, when $R^9$ represent a nitro group, suitable conversions of the nitro group into another group $R^9$ include the following:
(i) converting the nitro group into a halogen atom;
(ii) converting the nitro group into an amine group;
(iii) converting the nitro group into a halogen atom followed by conversion of the halogen atom into the above defined group $—NR^sR^t$;
(iv) converting the nitro group into an amino group and thereafter alkylating the amino group to provide the above defined group $—NR^sR^t$; and
(v) converting the nitro group into a halogen atom, then converting the halogen atom into an alkoxy group.

A nitro group may be converted into a halogen atom by using any convenient halogenating agent.

One suitable halogenating agent is a hydrogen halide, suitably reacted in aqueous conditions for example by using concentrated hydrochloric acid at an elevated temperature, for example in the range of from 50° to 150° C.

A further suitable halogenating agent is a phosphorous oxyhalide, such as phosphorous oxychloride or phosphorous oxybromide, which may be reacted in any suitable solvent, such as dimethylformamide, suitably at an elevated temperature for example in the range of from 50° C. to 150° C.

A nitro group may conveniently be converted into an amino group by conventional reduction methods for example by using tin powder and concentrated hydrochloric acid at ambient temperature or by using sodium dithionite in aqueous methanol at ambient temperature.

When $R^9$ in the compound of formula (II) represents a halogen atom it may be converted into a group $—NR^sR^t$ by reacting with a reagent of formula (X):

$$HNR^sR^t \qquad (X)$$

wherein $R^s$ and $R^t$ are as defined above.

The reaction between the compound of formula (II) and the compound of formula (X) may be carried out in any suitable solvent, such as toluene, at any temperature providing a convenient rate of formation of the product, but suitably at an elevated temperature, such as in the range of from 50° to 180° C., at atmospheric or an elevated pressure.

Suitable alkylation methods for use in the abovementioned conversions include those used conventionally in the art, for example methods using halides, preferably iodides, in the presence of a base such as potassium carbonate in any convenient solvent for example acetonitrile or toluene; and if necessary using appropriate protecting procedures discussed herein.

In the conversion (v), the nitro group may be converted into the halogen atom as described above. The conversion of the halogen atom into an alkoxy group may be effected by any conventional alkoxylation procedure, for example treating the halogen with a source of alkoxy ions, such as a sodium alkoxide.

A compound of formula (II) may also be prepared according to methods disclosed in EP 0389282.

A compound of formula (VIII) may be prepared according to methods disclosed in EP 0369744.

A compound of formula (IV), wherein $R^{10}$ is alkyl or a benzyl group substituted or unsubstituted in the phenyl ring, may be prepared by reacting an activated form of a compound of formula (XI):

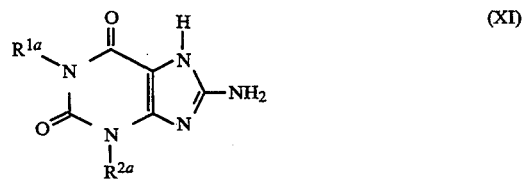

wherein $R^{1a}$ and $R^{2a}$ are as defined in relation to formula (I), with a compound of formula (XII):

$$R^{13}L^4 \qquad (XII)$$

wherein $R^{13}$ is alkyl or a benzyl group substituted or unsubstituted in the phenyl ring and $L^4$ represents a leaving group, such as a halogen atom, for example a bromine or chlorine atom.

The reaction between the compounds of formulae (XI) and (XII) may be carried out under conventional alkylation or benzylation conditions, for example in a solvent such as dimethylformamide, tetrahydrofuran of dimethoxyethane at any suitable temperature providing a suitable rate of formation of the product, suitably an elevated temperature, for example in the range of between 30° C. to 110° C.

A suitable activated form of a compound of formula (XI) is a salted form, in particular an alkali metal salted form, for example a potassium salted form.

The activated form of a compound of formula (XI) is prepared by the appropriate conventional procedure, for example that disclosed hereinbefore in relation to the activated form of a compound of formula (II).

A compound of formula (XI) and compounds of formula (IV) wherein $R^{10}$ is hydrogen may be prepared according to methods disclosed in EP 0389282.

The intermediate compounds of formulae IV (wherein $R^{10}$ is other than hydrogen) and (VI) are novel compounds and form a further part of the present invention.

The intermediate compounds of formulae (III), (VII), (X) and (XII) are known compounds or are prepared using methods used to prepare known compounds, for example those disclosed in Advanced Organic Chemistry, 3rd Edition (1985), Published by John Wiley and Sons.

Suitable values for $R^{1a}$ and $R^{2a}$ include $R^1$ and $R^2$ respectively or nitrogen protecting groups such as silyl groups.

When $R^{1a}$ or $R^{2a}$ represents other than $R^1$ or $R^2$ respectively, the abovementioned conversions of $R^{1a}$ into $R^1$ and $R^{2a}$ to $R^2$ may be carried out using the appropriate conventional procedure.

The protection of any reactive group or atom, such as the xanthine nitrogen atom may be carried out at any appropriate stage in the aforementioned process. Suitable protecting groups include those used conventionally in the art for the particular group or atom being protected, for example suitable protecting groups for the xanthine nitrogen atoms are alkylsilyl groups, especially trimethylsilyl or t-butyldimethylsilyl groups.

Protecting groups may be prepared and removed using the appropriate conventional procedure: For example, alkylsilyl protecting groups may be prepared by treating the compound of formula (II) with an appropriate alkylsilyl halide, for example trimethylsilyl chloride for trimethylsilyl groups and t-butyldimethylsilyl chloride for t-butyldimethylsilyl groups. The silyl protecting groups may be removed by treatment with t-butylammonium fluoride in a suitable solvent, such as tetrahydrofuran conveniently at an ambient temperature.

As mentioned above the compounds of the invention are indicated as having useful therapeutic properties: the present invention accordingly provides a compound of formula (I) or where appropriate a pharmaceutically acceptable salt thereof and/or a pharmaceutically acceptable solvate thereof, for use as an active therapeutic substance.

Thus the present invention provides a compound of formula (I) or where appropriate a pharmaceutically acceptable salt thereof and/or a pharmaceutically acceptable solvate thereof, for use in the treatment of and/or prophylaxis of disorders associated with increased numbers of eosinophils, such as asthma, and allergic disorders associated with atopy, such as urticaria, eczema and rhinitis.

In a further aspect the present invention also provides a compound of formula (I) or where appropriate a pharmaceutically acceptable salt thereof and/or a pharmaceutically acceptable solvate thereof, for use as a phosphodiesterase inhibitor.

In a particular aspect, as indicated hereinbefore, the present invention provides a compound of formula (I) or where appropriate a pharmaceutically acceptable salt thereof and/or a pharmaceutically acceptable solvate thereof, for use in the treatment of disorders of the respiratory tract, such as reversible airways obstruction and asthma.

In a further particular aspect, the present invention provides a compound of formula (I) or where appropriate a pharmaceutically acceptable salt thereof and/or a pharmaceutically acceptable solvate thereof, for use in the treatments mentioned hereinbefore, such as cerebral vascular and neuronal denerative disorders associated with learning, memory and cognitive dysfunctions, peripheral vascular disease or proliferate skin disease or for the prophylaxis of disorders associated with neuronal degeneration resulting from ischaemic events or for the inhibition of the production of tumour necrosis factor in for example the treatment of human immunodeficiency virus.

A compound of formula (I) or where appropriate a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention provides a pharmaceutical composition comprising a compound of formula (I) or where appropriate a pharmaceutically acceptable salt thereof and/or a pharmaceutically acceptable solvate thereof, and a pharmaceutically acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral, intravenous or intramuscular administration or through the respiratory tract. Preparations may be designed to give slow release of the active ingredient.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators, for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (I), or if appropriate a pharmaceutically acceptable salt thereof and/or a pharmaceutically acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (I) or if appropriate a pharmaceutically acceptable salt thereof, are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound of formula (I), or if appropriate a pharmaceutically acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day; and such therapy may extend for a number of weeks or months.

When used herein the term 'pharmaceutically acceptable' encompasses materials suitable for both human and veterinary use. No toxicological effects have been established for the compounds of formula (I) in the above-mentioned dosage ranges.

The following pharmacological data and examples illustrate the invention. The following preparations illustrate the preparation of intermediates to the novel compounds of formula (I).

Example 1

8-Amino-7-benzenesulphonyl-1,3-di(cyclopropylmethyl)xanthine

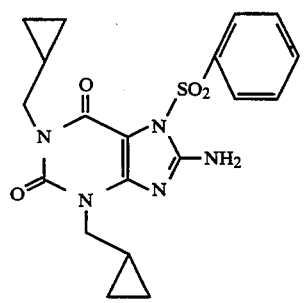

Potassium t-butoxide (0.12 g, 1.1 mmole) was added to a suspension of 8-amino-1,3-di(cyclopropylmethyl) xanthine (0.27 g, 1 mmole) in dimethoxyethane (4 ml) and the resulting mixture was stirred at ambient temperature for 2 hr. Benzenesulphonyl chloride (0.35 g, 2 mmol)

was added and the mixture was stirred at ambient temperature for 18 hr, then at 80° C. for 6 hr. After cooling, the reaction mixture was added to ethyl acetate (100 ml), washed with water (50 ml) and dried (MgSO$_4$). Removal of the solvent at reduced pressure gave a solid (0.5 g) which was chromatographed on silica (acetone/hexane 1:3) to give 8-amino-7-benzensulphonyl-1,3-di(-cyclopropylmethyl)xanthine (0.18 g, 43%) m.p. 170°–1° C. $\nu_{max}$ (KBr) 3457(w), 3434(w), 1704(m), 1653(s) and 1500(s)cm$^{-1}$;

$^1$H NMR δ(CDCl$_3$): 0.34–0.52 (8H,m), 1.16–1.31 (2H,m), 3.82(4H,d,J=7.15 H$_z$). 6.36 (2H, brs), 7.58 (2H,t, J=8.0 H$_z$), 7.69 (1H,t,J=7.0 Hz), 8.21 (2H,d,J=7.0 H$_z$).

m/e 154 (100%), 136(75), 55(50), 391(30).

Found C, 54.85; H, 5.19; N, 16.90; S, 7.55. C$_{19}$H$_{21}$N$_5$O$_4$S requires C, 54.92; H, 5.10; N, 16.86; S, 7.72%.

The following compounds in Examples 2–13 were prepared using an analogous method to that disclosed in Example 1.

Example 2

8-Amino-1,3-di(cyclopropylmethyl)-7-(4-methoxybenzenesulphonyl)xanthine

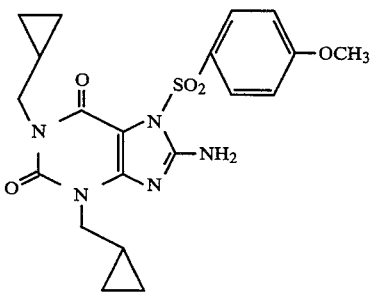

37% m.p. 177°–8° C,. $\nu_{max}$ (KBr) 3450 (m), 1705 (m), 1646 (s), 1594 (m) and 1499 (s) cm$^{-1}$ $^1$H NMR δ(CDCl$_3$): 0.32–0.51 (8H, m), 1.15–1.35 (2H, m), 3.82 (2H, d, J=4.5 Hz), 3.84 (2H, d, J=4.5 Hz), 3.88 (3H, s), 6.34 (2H, brs), 7.01 (2H, d, J=9.0 Hz), 8.16 (2H, d, J=9.0 Hz);

m/e 244 (100%), 55 (25), 137 (21), 155 (15), 247 (14.5), 220 (14), 445 (M+, 13);

Found C, 53.73; H, 5.07; N, 15.39; S, 7.08. C$_{20}$H$_{23}$N$_5$O$_5$S requires C, 53.92; H, 5.20; N, 17.72; S, 7.20%.

Example 3

8-Amino-1,3-di-(cyclopropylmethyl)-7-(3,4-dimethoxy-benzenesulphonyl)xanthine

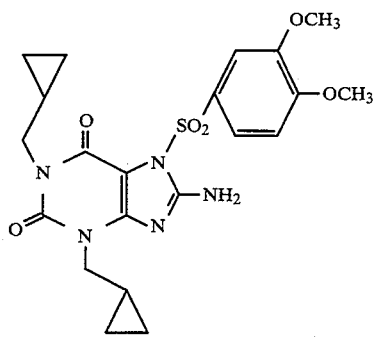

31%, m.p. 183°4° C.

$^1$H NMR δ(CDCl$_3$): 0.4–0.52 (8H, m) 1.19–1.29 (2H, m), 3.85 (4H, overlapping dd, J:7.7 H$_z$) 3.96 (3H, s), 3.98 (3H, s), 6.28 (2H, brs), 6.97 (1H, d, J=8.8 H$_z$), 7.78 (1H, dd, J=8.8, 2.2 H$_z$), 7.98 (1H, d, J=2.2 H$_z$);

m/e 476 (MH+, 100%), 274 (86), 55 (50);

Found C, 53.03; H, 5.13; N, 14.68; S, 6.74.C$_{21}$H$_{25}$N$_5$O$_6$S requires C, 55.04; H, 5.30; N, 14.73; S, 6.74%

Example 4

8-Amino-1.3.di(cyclproylmethyl)-7-(2,5-dimethoxy-benzenesulphonyl)xantine

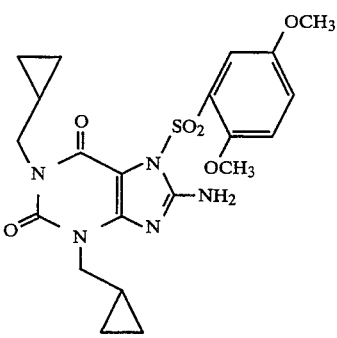

33%, m.p. decomposed >200° C.

$^1$H NMR δ(CDCl$_3$): 0.25–0.37 (4H, m), 0.39–0.53 (4H, m), 1.11–1.19 (1H, m), 1.22–1.32 (1H, m), 3.75 (2H, d, J=7.15 Hz), 3.84 (2H, d, J=6.6 Hz), 3.82 (3H, s), 3.89 (3H, s), 6.50 (2H, brs), 6.91 (1H, d, J=9.0 Hz), 7.17 (1H, dd, J=9.0 Hz) 7.87 ( 1H, d, J=3.3 Hz);

m/e 154 (100%), 136 (75), 476 (MH+, 37), 391 (30), 69 (27), 107 (25), 274 (24);

Found C, 52.75; H, 5.48; N, 14.73, S, 6.51; C$_{21}$H$_{25}$N$_5$O$_6$S requires C, 53.04; H, 5.30; N, 14.73; S, 6.74%.

Example 5

8-Amino-1,3-di(cyclopropylmethyl)-7-(2-methoxy-5-bromo-benzenesulphonyl)xanthine

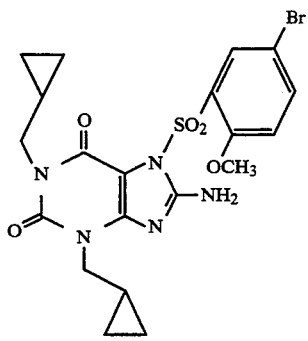

38%, m.p. decomposes >190° C.

¹H NMR δ(CDCl₃): 0.15–0.49 (8H, m), 0.96–1.02 (1H, m), 1.18–1.24 (1H, m), 3.58 (2H, d, J=6–85 Hz), 3.76 (2H, d, J=7.15 Hz). 3.82 (3H, s), 7.23 (1 d, J=9.10 Hz), 7.90 (1H, dd, J=9.10 Hz, 2.75 Hz), 7.90 (2H, brs), 8.14 (1H, d, J=2.50 Hz) m/e 176 (100%), 413 (45), 329 (30), 391 (28), 107 (24), 307 (19), 524 (MH⁺, 10), 526 (MH⁺, 10);

Found C, 45.86; H, 4.25; N, 13.30; S, 6.08;C₂₀H₂₂BrN₅O₅S Requires C, 45.81; H, 4.23; N, 13.36%; S 6.11%.

Example 6

8-Amino-1,3-di(cyclopropylmethyl)-7-(4-tri-fluoromethylbenzenesulphonyl)xanthine

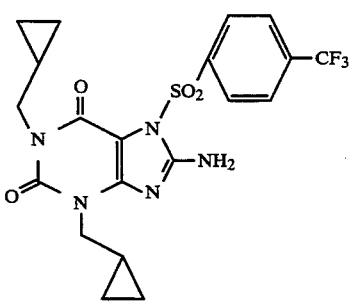

35%, m.p. 207°–208° C.

¹H NMR δ(CDCl₃): 0.31–0.52 (8H, m), 1.13–1.59 (2H, m), 3.81 (2H, s, J=5.5 Hz), 3.83 (2H, d, J=5.5 Hz), 6.25 (2H, brs), 7.84 (2H, d, J=8.25 Hz), 8.36 (2H, d, J=8.25 Hz); 434 (MH⁺, 100%), 274 (65), 55 (38).

Example 7

8-Chloro-1,3-di(cyclopropylmethyl)-7-(4-methoxybenzenesulphonyl)xanthine

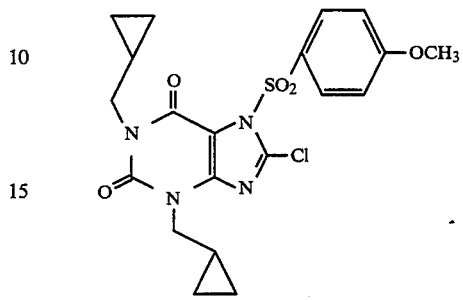

32%, m.p. 118.20° C,. ν$_{max}$ (KBr) 3063 (m), 2903 (m), 1708 (s), 1650 (s), 1600 (m), 1545 (m), 1499 (m), 1465 (m) and 1394 (m) cm⁻¹;

¹H NMR δ(CDCl₃): 0.40–0.53 (8H, m), 1.19–1.36 (2H, m), 3.90 (3H, s), 3.89–3.92 (4H, m), 7.06 (2H, d, J=9.1 Hz), 8.34 (2H, d, J=9.1 Hz):

m/e 464 (+, 30%), 171 (100);

Found C, 51.33; H, 4.47; N, 11.98; C₂₀H₂₁N₄O₅SCl requires C, 51.66; H, 4.55; N, 12.05%.

Example 8

1,3-Di(cyclopropylmethyl)-7-(4-methoxybenzenesulphonyl)-8-phthalimido)xanthine

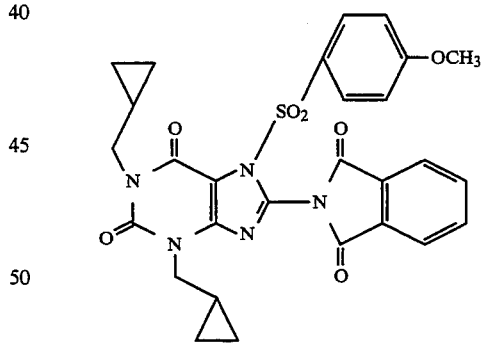

66%; m.p. 214°–6° C.; ν$_{max}$ (KBr) 1745 (s), 1715 (m), 1672 (s), 1488 (s), 1370 (s), 1268 (m), 1173 (m) and 589 (m) cm⁻¹;

¹H NMR δ(CDCl₃: 0.37–0.55 (8H, m), 1.19–1.32 (2H, m), 3.87 (2H, d, J=7.15 Hz), 3.89 (3H, s), 3.97 (2H, d, J=7.40 Hz), 7.02 (2H, d, J=9.35 Hz), 7.89 (2H, m), 8.05 (2H, m), 8.26 (2H, d, J=9.10 Hz);

m/e 406 (100%), 155 (40), 423 (23), 576 (MH⁺, 15).

Found C, 58.12; H, 4.37; N, 12.16; S, 5.46; C₂₈H₂₅N₅O₇S requires C, 58.42; H, 4.38; N, 12.17; S, 5.56%.

Example 9

8-Amino-1,3-di(cylcopropylmethyl)-7-(4-chlorobenzenesulphonyl)xanthine

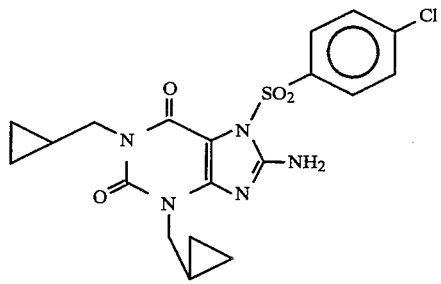

Yield 29%, m.p. 181°–183° C.

$v_{max}$ (KBr) 3442 (s), 1705 (m), 1645 (s) 1498 (s) and 637 (m) cm$^{-1}$.

$^1$H NMR δ(CDCl$_3$): 0.35–0.52 (8H,m), 1.16–1.28 (2H,m), 3.81 (2H, d, J=1.1 Hz), 3.84 (2H, d, J=1.4 Hz), 6.24 (2H, br s), 7.54 (2H, d, J=8.8 Hz), 8.17 (2H, d, J=9.1 Hz)

m/e 450 (MH$^+$, 20%), 277 (70), 215 (44), 135 (100), 123 (50), 93 (100).

Found C, 50.72; H, 4.48; N 15.57; S, 7.13, Cl 17.88. C$_{19}$H$_{20}$ClN$_5$O$_4$S requires, C, 50.73; H, 4.43; N, 15.58; S, 7.12; Cl, 7.89%.

Example 10

1,3-Di(cyclopropylmethyl)-7-(4-methoxybenzenesulphonyl)xanthine

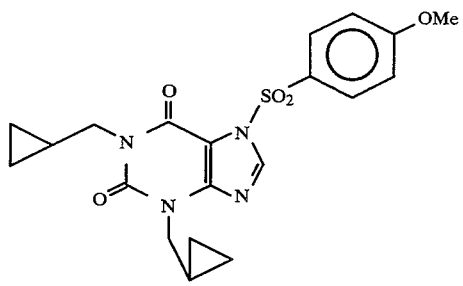

64%, 123°–4° C.

$v_{max}$ (KBr) 3434 (m), 1711 (s), 1667 (s) and 1171 (s) cm$^{-1}$.

$^1$H NMR δ(CDCl$_3$): 0.39–0.54 (8H,m), 1.21–1,32 (2H,m), 3.86–3.98 (7H,m), 7.03 (2H, d, J=9.1 Hz), 8.23 (2H, d, J=9.1 Hz), and 8.27 (1H,s).

m/e 431 (MH$^+$, 65%), 171 (100), 155 (15), 107 (45) and 55 (45).

Example 11

8-Amino-1,3-di(cyclopropylmethyl)-7-(4-methylbenzenesulphonyl)xanthine

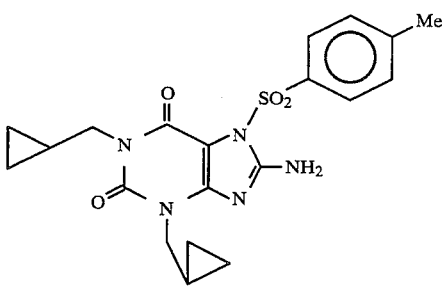

30%, 182°–183° C.

$v_{max}$ (KBr) 3454 (m), 1706 (s), 1636 (s), 1599 (s), 1498 (s) and 667 (m) cm$^{-1}$.

$^1$H NMR δ(CDCl$_3$): 0.37–0.51 (8H,m), 1.16–1.29 (2H,m), 2.45 (3H,s), 3.81 (2H, d, J=2.2 Hz), 3.84 (2H, d, J=2.2 Hz), 6.32 (2H, br s), 7.36 (2H, d, J=7.98 Hz), 8.09 (2H, d, J=8.52 Hz).

m/e 430 (MH$^+$, 30), 277 (60), 215 (59), 185 (100) and 75 (98).

Found C, 55.85; H, 5.01; N, 16.30; S, 7.34. C$_{20}$H$_{23}$N$_5$O$_4$S requires C, 55.93; H, 5.40; N, 16.31; S, 7.46%

Example 12

8-Amino-1,3-di(cyclopropylmethyl)-7-(2-carbomethoxybenzenesulphonyl)xanthine

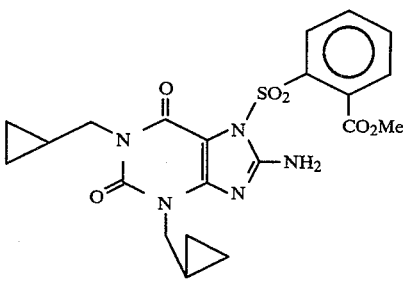

m.p. 167°–169° C.

$^1$H NMR δ(CDCl$_3$): 0.22–0.50 (8H,m), 1.13–1.29 (2H,m), 3.70 (2H, d, J=7.5 Hz), 3.86 (2H, d, J=7.15 Hz), 3.93 (3H,s), 6.20 (2H, br s), 7.72–7.78 (3H, m), 8.70–8.82 (1H,m).

Found C, 53.27; H, 4.90; N, 14.79; C$_{21}$H$_{23}$N$_5$O$_6$S requires C, 53.28; H, 4.86; N, 14.80%.

Example 13

8-Amino-1,3-di(cyclopropylmethyl)-7-(3-trifluoromethylbenzene-sulphonyl)-xanthine

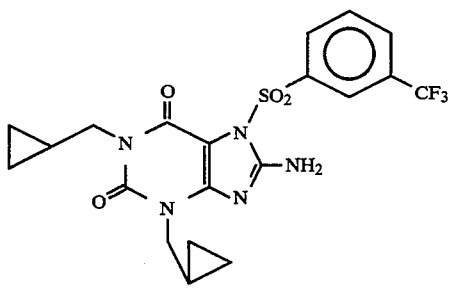

37%, m.p. >170° C. (d).

$\nu_{max}$ (KBr) 3450 (s), 1706 (s), 1659 (s), 1498 (s) and 1378 (m).cm$^{-1}$.

$^1$H NMR δ(CDCl$_3$): 0.31–0.52 (8H, m), 1.11–1.32 (2H, m), 3.81 (2H, d, J=2.75 Hz), 3.84 (2H, d, J=2.75 Hz), 6.27 (2H, brs), 7.71–7.78 (1H, m), 7.93–7.96 (1H, m), 8.48–8.51 (2H, m).

m/e 484 (MH+, 11%), 276 (32%).

Found C, 49.83; H, 4.36; N, 14.46; S, 6.64. C$_{20}$H$_{20}$N$_5$O$_4$F$_3$S requires C, 49.68; H, 4.17; N, 14.49; S, 6.63%.

Example 14

8-Amino-1,3-di(cylopropylmethyl)-7-(isopropylsulphonyl)xanthine

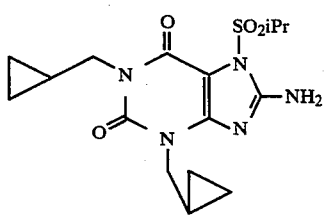

Sodium hydride (0.35 g of a 60% suspension in oil, 8.7 mmol) was added to a suspension of 8-amino-1,3-di(cyclopropylmethyl)xanthine (2 g, 7.3 mmol ) in dimethoxyethane (40 ml) and the resulting mixture stirred at ambient temperature for 2 hr. Isopropylsulphonyl chloride (1.24 g, 8.7 mmol) was added and the mixture was heated at reflux for 18 hours. The reaction mixture was allowed to cool and then water (1 ml) was added dropwise. The mixture was added to ethyl acetate (200 ml), washed with water (50 ml) and dried (MgSO$_4$). The solvent was removed at reduced pressure to afford the crude residue which was chromatographed on silica (acetone/hexane 1:3) to afford 8-amino-1,3-di(cylcopropylmethyl )-7-(isopropylsulphonyl)xanthine (1.25 g, 45%) as a yellow foam. Recrystallisation from ethyl acetate/hexane afforded a white flocculent solid, m.p. 119°–120° C.

$\nu_{max}$(KBr) 3461 (m), 3320 (m), 1702 (s), 1652 (s), 1602 (m), 1500 (s), 1379 (m), 1357 (m), 1277 (m), 1174 (m) and 698 (m) cm$^{-1}$.

$^1$H NMR δ(CDCl$_3$): 0.21–0.55 (8H, m), 1.26–1.35 (2H, m), 1.50 (6H, d, J=6.9 Hz), 3.88 (2H, d, J=7.1 Hz), 3.89 (2H, d, J=7.1 Hz), 4.75 (1H, septet, J=6.9 Hz), 6.09 (2H, br s).

m/e 382 (MH+, 100%)

Found 382.1544. C$_{16}$H$_{24}$N$_5$O$_2$S (MH+) Requires 382.1549

Example 15

8-Amino-1,3-di(cyclopropylmethyl)-7-(methanesulphonyl)xanthine

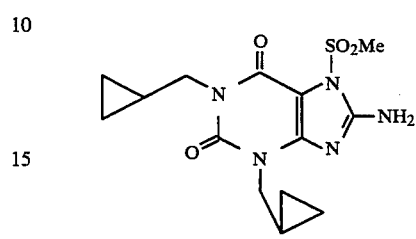

8-Amino-1,3-di(cyclopropylmethyl)-7-(methanesulphonyl)xanthine was prepared according to the procedure of Example 14. using methanesulphonyl chloride 19% m.p. 201°–202° C., $\nu_{max}$ (KBr) 3457 (w), 3432 (w), 1701 (m), 1645 (s), 1502 (s), 1355 (m), 1274 (m), 1172 (m), and 756 (w) cm$^{-1}$.

$^1$H NMR δ(CDCl$_3$): 0.41–0.55 (8H, m), 1.26–1.33 (2H, m), 3.85 (3H, s), 3.88 (2H, d, J:7.4 Hz), 3.89 (2H, d, J:7.2 Hz), 6.12 (2H, br s).

m/e 364 (MH+, 100%)

Found C, 47.64; H, 5.71; N, 19.61. C$_{14}$H$_{19}$N$_5$SO$_4$ requires C, 47.57; H, 5.42; N, 19.82%

Example 16

8-Amino-1,3-di-(cyclopropylmethyl)-7-(3,5-bis-(trifluoromethyl) benzenesulphonyl)xanthine

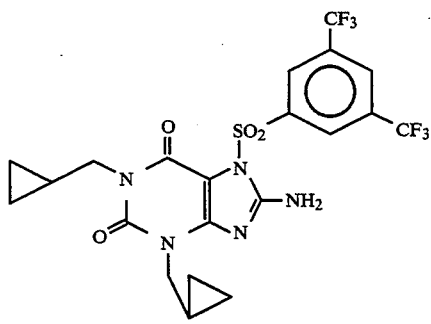

The compound was prepared according to the procedure of Example 1. 21% m.p. 168°–169° C.

$\nu_{max}$ (mmol) 3450 (s), 3100 (m), 1710 (s), 1660 (s), 1500 (s), 1280, 1200, 1140,750, 690 and 640 cm$^{-1}$.

$^1$H NMR δ(CDCl$_3$): 0.35–0.53 (8H, m), 1.13–1.29 (2H,m), 3.80–3.84 (4H,m), 6.36 (2H, br s), 8.18 (1H, s) and 8.78 (2H,s).

Found C, 45.82; H, 3.47; N, 12.67; C$_{21}$H$_{19}$F$_6$N$_5$O$_4$S requires C, 45.74; H, 3.45; N, 12.70%.

Examples 17 and 18

8-Amino-1,3-di(cyclopropylmethyl)-7-(4-nitrobenzenesulphonyl)xanthine (Example 17) and 1,3-di(cyclopropylmethyl)-8-[di(4-nitrobenzenesulphonyl)amino]xanthine (Example 18)

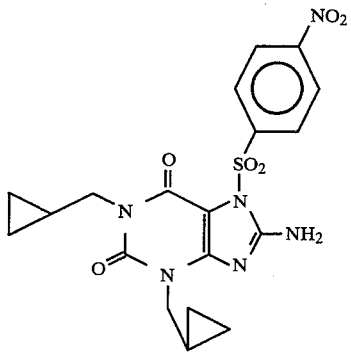

Example 17

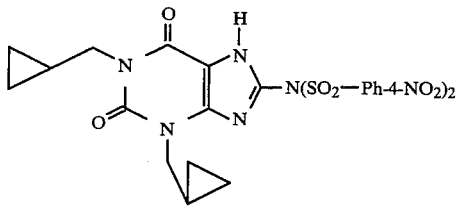

Example 18

8-Amino-1,3-di(cyclopropylmethyl)xanthine (2.7 g, 10 mmol), 4-nitrobenzenesulphonyl chloride (5.5 g, 25 mmol) and triethylamine (3 ml, 20 mmol) were stirred together in tetrahydrofuran (THF) (40 ml) at ambient temperature for 24 hr. After adding to water (100 ml) the mixture was extracted into ethyl acetate (150 ml) and the organic solution dried (MgSO$_4$) and evaporated. Chromatography of the residue on silica, (hexane/acetone gradient) gave 8-amino- 1,3-di(cyclopropylmethyl)-7-(4-nitrobenzenesulphonyl)xanthine followed by 1,3-di(cyclopropylmethyl)-8di(cyclopropylmethyl)-8-di(4-nitrobenzenesulphonyl)aminoxanthine.

Example 17

(0.77 g, 17%) m.p. 188°-9° C,. $\nu_{max}$ (KBr) 3442 (w), 1709 (m), 1646 (s) and 1501 (s) cm$^{-1}$;

$^1$H NMR $\delta$(CDCl$_3$): 0.34-0.52 (8H, m), 1.15-1.25 (2H, m), 3.81 (4H, t (overlapping d), J=7.5 Hz), 6.35 (2H, br s), 8.42 (4H, ABq, J=9.5, 1 Hz);

m/e 276 (100%), 397(7), 247 (6) and 461 (M+, 5);

Found C, 49.55; H, 4.18; N, 18.32; S, 6.79, C$_{19}$H$_{20}$N$_6$O$_6$S requires C, 49.56; H, 4.38; N, 18.25; S, 6.96%.

Example 18

(1.5 g, 23% ) m.p. 198° C,. $\nu_{max}$ (KBr) 1705 (s), 1646 (s) and 1534 (s) cm$^{-1}$;

$^1$H NMR $\delta$(CDCl$_3$): 0.35-0.57 (8H, m), 1.20-1.40 (2H, m), 3.67 (2H, d, J=7.0 Hz), 3.95 (2H, d, J=7.0 Hz), 8.38 (8H, ABq, J=8.5, 3.5 Hz);

m/e 252 (100), 55 (65), 461 (57), 73 (43), 170 (47), 181 (40);

Found C, 46.27; H, 3.17; N, 14.88; C$_{25}$H$_{23}$N$_7$O$_{10}$S requires C, 46.51; H, 3.59: N, 15.19%.

Examples 19 and 20

8-Amino-1,3-di(cyclopropylmethyl)-7-(4-methoxybenzenesulphonyl)xanthine (Example 19) and 1,3-di(cyclopropylmethyl)-8-[di(4-methoxybenzenesulphonyl)amino]xanthine (Example 20)

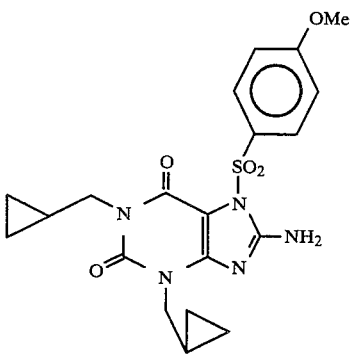

Example 19

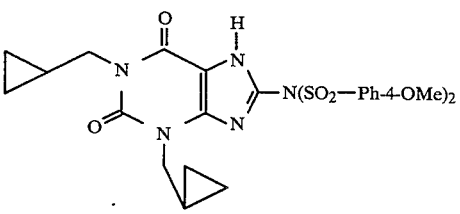

Example 20

8-Amino-1,3-di(cyclopropylmethyl)xanthine (1.35 g, 5 mmol), 4-methoxybenzene-sulphonyl chloride (2.06 g, 10 mmol)and triethylamine (1.01 g, 1.4 ml, 10 mmol) were stirred together in THF (40 ml) at reflux for 48 hr. After cooling, the solvent was removed under reduced pressure and the residue chromatographed on silica (hexane/acetone gradient) to give 4-methoxybenzenesulphonyl chloride (0.643 g, 31%), followed by 8-amino-1,3-di(cyclopropylmethyl)-7-(4-methoxybenzenesulphonyl)xanthine followed by 1,3-di(cyclopropylmethyl)-8-[di-(4-methoxybenzene-sulphonyl)amino]xanthine (0.47 g, 15%).

Example 19

(0.15 g, 6.7%) m.p. 177°-8° C.

$\nu_{max}$(KBr) 3450 (m), 1705 (m), 1646 (s), 1594 (m) and 1499 (s) cm$^{-1}$;

$^1$H NMR $\delta$(CDCl$_3$): 0.32-0.51 (8H, m), 1.15-1,35 (2H, m), 3.82 (2H, d, J=4.5 Hz), 3.84 (2H, d, J=4.5Hz), 3.88 (3H, s), 6.34 (2H, br s), 7.01 (2H, d, J=9.0 Hz) and 8.16 (2H, d, J=9.0 Hz);

m/e 244 (100%), 55 (25), 137 (21), 155 (15), 247 (14.5), 220 (14), 445 (M+, 13);

Found C, 53.73; H, 5.07; N, 15.39; S, 7.08; C$_{20}$H$_{23}$N$_5$O$_5$S requires C, 53.92; H, 5.20; N, 17.72; S, 7.20%

Example 20 m.p. 220°-225° C. (d)

$\nu_{max}$ (KBr) 1702 (s), 1647 (s), 1595 (s)and 1497 (s)cm$^{-1}$;

$^1$H NMR $\delta$(CDCl$_3$): 0.33-0.46 (8H, m), 1.14-1.20 (2H, m), 3.78 (4H, t, (overlapping d) J=8.0 Hz), 3.90 (6H, s), 7.15 (4H, d, J=9.0 Hz), 7.85 (4H, d, J=7.5 Hz), 14.70 (1H, br);

m/e 93 (100%), 185 (100), 277 (50), 57 (47), 616 (M+, 35), 446 (40).

Found C, 52.28; H, 4.91; N, 11.00; $C_{27}H_{29}N_5O_8S_2$ requires C, 52.67; H, 4.75; N, 11,38%.

Example 21

1,3-Di(cyclopropylmethyl)-8-[di(benzenesulphonyl)amino]xanthine

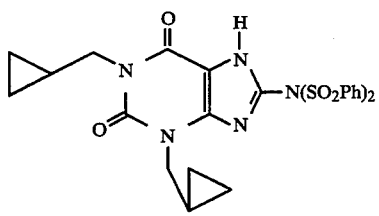

8-Amino-1,3-di(cyclopropylmethyl)xanthine (0.27 g, 1 mmol) and benzenesulphonyl chloride (0.34 g, 2 mmol) were stirred together in pyridine (4 ml) at ambient temperature. After stirring for 48 hr the mixture was added to ethyl acetate (150 ml), washed with dilute hydrochloric acid (2×50 ml), water (50 ml) and dried (MgSO$_4$). Removal of the solvent under reduced pressure gave a solid (0.48 g) which was chromatographed on silica (acetone/hexane gradient) to give 1,3-di (cyclopropylmethyl)-8-[di(benzenesulphonyl)amino]xanthine, (0.33 g, 59%) m.p. 238° C.

$v_{max}$ (KBr) 1708 (s), 1651 (s), 1557 (m), 1485 (s), 1189 (s), 887 (s), 546 (s) cm$^{-1}$,.

$^1$H NMR δ(CDCl$_3$): 0.41–0.58 (8H, m), 1.17–1.43 (2H, m), 3.80 (2H, d, J=7.15 Hz), 3.98 (2H, d, J=7.15 Hz), 7.48–7.68 (6H, m), 7.99 (4H, d, J=7.4 Hz), 13.25 (1H, br)

m/e 555 (M+, 5%), 415 (40), 386 (10)

Analysis: Found C, 53.84; H, 4.46; N, 12.60; S, 11,36. $C_{25}H_{25}N_5O_6S_2$ requires C, 54.04; H, 4.54; N, 12.61; S, 11.54%

Example 22

1,3-Di(cyclopropylmethyl)-8-di(4-methoxybenzenesulphonyl)amino-7-(4-methoxybenzyl)xanthine

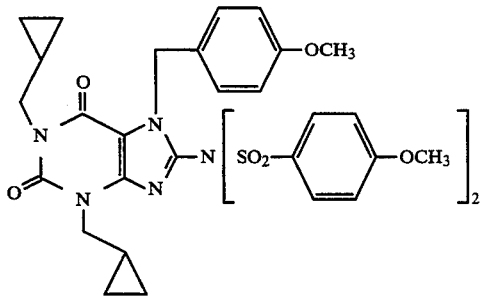

Potassium t-butoxide (0.35 g, 3 mmole) was added to a solution of 8-amino-1,3-di(cyclopropylmethyl)-7-(4-methoxybenzyl)xanthine (0.99 g, 2.5 mmole) in dimethoxyethane (10 ml) and the resulting solution was stirred for 3 hr. at ambient temperature. A solution of 4-methoxybenzenesulphonyl chloride (0.77 g, 3.75 mmole) in dimethoxyethane (3 ml) was slowly added over 5 min. to the dark solution to give a precipitate. After stirring for 48 hr. at ambient temperature the mixture was added to ethyl acetate (150 ml), washed with water (50 ml) and dried (MgSO$_4$). Removal of the solvent at reduced pressure gave a solid which was chromatographed on silica (acetone/hexane, gradient) to give:- 1,3-di(cyclopropylmethyl)-8-di(4-methoxybenzenesulphonyl )amino-7-(4-methoxybenzyl)xanthine (0.36 g, 20%). m.p. 182°–3° C.

$v_{max}$ (KBr) 1705 (s), 1660 (s), 1594 (s), 1172 (s) and 550 (s) cm$^{-1}$;

$^1$H NMR δ(CDCl$_3$): 0.35–0.51 (8H, m), 1.25–1.28 (2H, m), 3.78 (3H, s). 3.88 (6H, s), 3.88 (4H, t(overlapping d), J=7.0 Hz, 5.50 (2H, s), 6.82 (4H, d, J=9.0 Hz), 6.88 (2H, d, J=9.0 Hz) 7.27 (2H, d, J=9.0 Hz), 7.69 (4H, d, J=9.0 Hz);

m/e 121 (100%), 155 (55), 564 (50), 735 (M+, 45), 172 (30);

Found C, 57.19; H, 4.95; N, 9.57; S, 8.61. $C_{35}H_{37}N_5O_9S_2$ requires C, 57.13; H, 5.07; N, 9.52; S, 8.71%.

Example 23

1,3-Di(cyclopropylmethyl)-8-di(benzenesulphonyl)amino-7-(4-methoxy-benzyl)xanthine

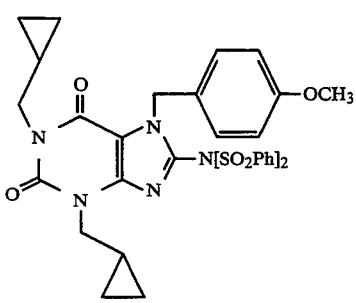

Following the method of Example 1, 1,3-di(cyclopropylmethyl)-8-di(benzenesulphonyl )amino-(4-methoxybenzyl)xanthine was prepared. 18.5%; m.p. 183° C.;

$v_{max}$ (KBr) 1703 (s), 1658 (s), 1541 (m), 1174 (s), 871 (s), 547 (s)cm$^{-1}$;

$^1$H NMR δ(CDCl$_3$): 0.41–0.52 (8H, m), 1.23–1.57 (2H, m), 3.79 (3H, s), 3.83 (2H, d, J=7.15 Hz), 3.90 (2H, d, J=7.15 Hz), 5.50 (2H, s), 6.88 (2H, d, J=8.50 Hz), 7.26–7.42 (6H, m), 7.63 (2H, t, J=7.5 Hz), 7.75 (4H, d, J=7.4 Hz)

m/e 176 (100%), 413 (40), 329 (35), 121 (25), 77 (15), 676 (MH+, (3.5), 557 (3.5).

Found C, 58.94; H, 5.05; N, 10.44; S, 9.16; $C_{33}H_{33}N_5O_7S_2$ requires C, 58.65; H, 4.92; N, 10.36; S, 9.49%.

Example 24

1,3-Di(cyclopropylmethyl)-8-(4-methoxybenzene-sulphonamido)-7-(4-methoxybenzyl)xanthine

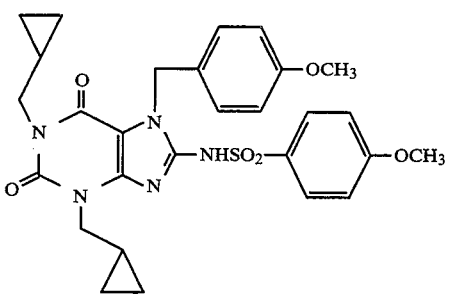

Potassium t-butoxide (0.75 g, 2.2 eq) was added to a solution of 8-amino-1,3-di(cyclopropylmethyl)-7-(4-methoxybenzyl)xanthine (1.17 g, 3 mmole) in dimethoxyethane (12 ml) and the resulting solution was stirred for 3 hr. at ambient temperature. 4-Methoxybenzenesulphonyl chloride (0.76 g, 1 eq) was added to the dark solution. After stirring for 24 hr at 60° C., the mixture was added to ethyl acetate (200 ml), washed with dil HCl (50 ml), water (50 ml) and dried (MgSO4). Removal of the solvent at reduced pressure gave a solid which was chromatographed on silica (acetone/hexane, gradient) to give:- 1,3-di(cyclopropylmethyl)-8-(4-methoxybenzene-sulphonamido)-7-(4-methoxybenzyl)xanthine (1.08 g, 64%), m.p 187° C.;

$^1$H NMR δ(CDCl$_3$): 0.37–0.63 (8H, m), 1.09–1.26 (2H, m), 3.75 (3H, s), 3.83 (2H, d, J:7.15 Hz), 3.87 (3H, s), 3.88 (2H, d, J=6.90 Hz), 5.32 (2H, brs), 6.74 (2H, d, J=8.50 Hz), 6.94 (2H, d, J:9.10 Hz), 7.37 (2H, d, J:8.80 Hz), 7.82 (2H, d, J=8.80 Hz).

m/e 121 (100%) 91 (60), 566 (MH+50), 232 (40).

Found C, 59.40; H, 5.46; N, 12.28; S, 5.34; C$_{28}$H$_{31}$N$_5$O$_6$S requires C, 59.45; H, 5.52; N, 12.38; S, 5.67%.

In a similar manner using appropriately 7-substituted 8-amino-1,3-di(cyclopropylmethyl)xanthines the following compounds were prepared.

Example 25

1,3-Di(cyclopropylmethyl)-8-(4-methoxybenzenesulphonami do)-7-(3,4,5-trimethoxybenzyl)xanthine

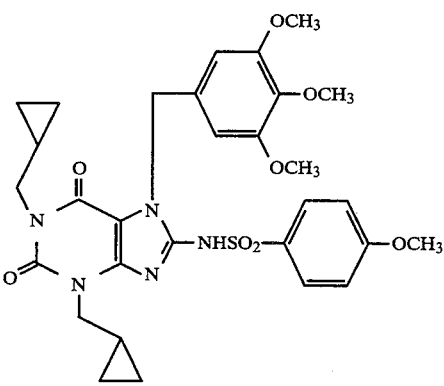

64%; m.p. 200°1° C.;

$v_{max}$(KBr) 3172 (w), 1700 (s), 1656 (s), 1596 (s), 1499 (m), 1463 (m), 1265 (m), 1129 (m) cm$^{-1}$;

$^1$H NMR δ(CDCl$_3$): 0.31–0.47 (8H, m), 1.2–1,3 (2H, m), 3.77 (3H, s), 3.78 (3H, s), 3.84 (4H, m), 3.86 (3H, s), 5.38 (2H, s), 6.82 (2H, s), 6.93 (2H, d, J=8.80 Hz), 7.87 (2H, d, J=9.10 Hz);

m/e 626 (MH+, 100%), 456 (80), 155 (25), 276 (8); MH+ observed 626.2227, C$_{30}$H$_{36}$N$_5$O$_8$S requires 626.2285.

Found C, 57.44, H, 5.62; N, 11.15; S, 4.96; C$_{30}$H$_{35}$N$_5$O$_8$S requires C, 57.59; H. 5.64; N, 11.19; S, 5.12%.

Example 26

1,3-Di(cyclopropylmethyl)-8-(4-methoxybenzenesulphonamido)-7-methyl xanthine

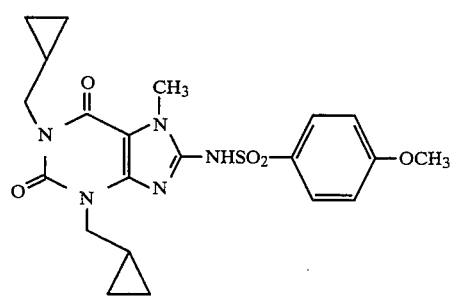

34%; m.p. 208°–9° C.;

$^1$H NMR δ(CDCl$_3$): 0.37–0.56 (8H, m), 1.12–1.27 (2H, m), 3.81 (3H, s), 3.84–3.89 (7H, m), 6.95 (2H, d, J=8.8 Hz), 7.83 (2H, d, J=8.8 Hz);

m/e 310 (100%), 178 (62), 290 (43), 460 (MH+, 41), 88 (36), 327 (34).

Example 27

8,Benzenesulphonamido-1,3-di(cyclopropylmethyl)-7-methylxanthine

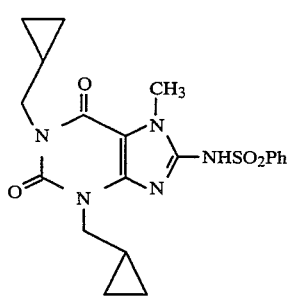

40.5% m.p. 163° C.;

$v_{max}$(KBr) 3223 (w), 1700 (m), 1662 (s), 1646 (s), 1457 (m), 1170 (m), 1090 (m) cm$^{-1}$;

$^1$H NMR δ(CDCl$_3$): 0.34–0.63 (8H, m), 1.08–1.29 (2H, m), 3.77 (3H, s), 3.86 (3H, s), 3.86 (4H, overlapping dd, J=7.15 Hz), 7.46–7.60 (3H, m), 7.89–7.93 (2H, m);

m/e 298 (100%), 429 (M+, 50), 55 (25), 234 (25).

Found C, 55.88; H, 5.12; N, 16.34; S, 7.15; C$_{20}$H$_{23}$N$_5$O$_4$S requires C, 55.93; H, 5.40; N, 16.31; S, 7.47%.

Example 28

1,3-Di(cyclopropylmethyl)-8-(4-methoxybenzenesulphonylamino)xanthine

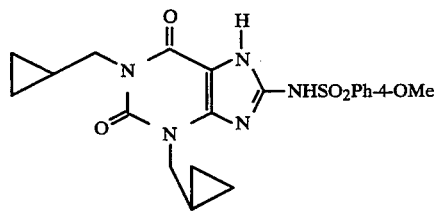

Sodium hydride (0.31 g of a 60% suspension in oil, 2.1 eq) was added to a suspension of 8-amino-1,3-di(cyclopropylmethyl)xanthine (1 g, 3.64 mmol) in tetrahydrofuran (25 ml). After 30 minutes, 4-methoxybenzenesulphonyl chloride (0.82 g, 1.1 eq) was added and stirring continued for 48 hours. The reaction mixture was poured into water, acidified with dilute hydrochloric acid and extracted into ethyl acetate. The combined organic solutions were dried (MgSO₄), filtered and concentrated. The crude residue was purified by column chromatography over silica in 2–5% methanol/dichloromethane to afford 1,3-di(cyclopropylmethyl)-8-(4-methoxybenzenesulphonylamino )xanthine (0.50 g, 31%) as a white solid m.pt>200° C. (decomp.)

$\nu_{max}$(KBr) 3414 (m), 3197 (m), 1702 (s), 1652 (s), 1597 (s), 1555 (m), 1464 (m), 1370 (s), 1185 (s) and 1092 (m) cm$^{-1}$;

$^1$H NMR δ(CDCl₃/d₆-DMSO): 0.21–0.43 (8H, m), 1.06–1.23 (2H, m), 3.70 (2H, d, J=6.9 Hz), 3.74 (2H, d, J=7.3 Hz), 3.82 (3H, s), 7.10 (2H, d, J=8.8 Hz), 7.81 (2H, d, J=9.2 Hz), 11.50 (1H, br s), 12.98 (1H, br s).

m/e Found 446.1498. $C_{20}H_{24}N_5O_5S$ (MH+) Requires 446.1498.

Pharmacological Data

Induction of blood eosinonhilia and the effects of drugs.

Animals

Male Charles River Sprague Dawley rats weighing between 270 to 400 g were used.

The method used was a modification of that described by Laycock et al (Int. Arch. Appl. Immunol, (1986). 81, 363).

Sephadex G200, particle size 40 to 120 micron, was suspended in isotonic saline at 0.5 mg/ml, and stored for 48 h at 4° C. 1 ml of the suspension was given intravenously to rats on days 0, 2 and 5. The test compound was given before the Sephadex on each occasion, with a contact time expected to give maximum activity at the time of the Sephadex administration. Blood was taken from the tail vein of the rats on day 7 for the determination of total and differential leucocyte counts.

A control group of at least 6 animals was included each time a compound was evaluated. The control group received Sephadex and the vehicle without test compound. The results in the drug treated animals were compared with the control group.

Total and differential leucocyte counts 20 ml samples of blood, taken from the tail vein of the rats, were added to 10 ml of Isoton II and, within 30rain, Zapoglobin (3 drops) was added, to lyse the erythrocytes. Five minutes later the total cell count was determined using a Coulter Counter Model DN. Differential leucocyte counts were carried out by fixing and staining a blood smear on a microscopic slide with May-Grunwald and Giemsa stains. A minimum of 400 cells were counted on each slide.

Statistics

Probability values were calculated using the Student's t test.

Results

The effect of the test compound upon Sephadex induced eosinophilia in the rat is set out below. The test compound was given orally 30 minutes before each injection of Sephadex.

| Test Compound (n = 16) | Dose mg/kg (orally-30 mins) | % of Control Mean ± SEM (n = 18) |
|---|---|---|
| Vehicle dosed control + sephadex i.v | — | 100 ± 17 |
| Example 2 | 50 | 51 ± 7** (n = 6) |
| | 20 | 62 ± 7* (n = 6) |

Notes
*$p < 0.05$
**$p < 0.01$

Inhibition of Phosphodiesterase

Isolation of phosphodiesterase

The $Ca^{2+}$/calmodulin-stimulated PDE (PDE I, see Table 1 and Beavo and Reifsynder (1990) for nomenclature) was prepared from bovine cardiac ventricle. Following chromatography on a Mono Q column, the fractions showing stimulation of PDE activity by $CA^{2+}$ and calmodulin were pooled and further purified on a calmodulin-affinity column. CGMP-stimulated PDE (PDE II), cG1VrP-inhibited PDE (PDE III) and cAMP-specific PDE (PDE IV) were all isolated from geinea-pig cardiac ventricle. Initial chromatography on a 20 ml Mono Q column resolved PDE III from a peak that contained both PDE II and PDE IV. The latter were separated by a cGMP-affinity column. The resolved PDEs were separately rechromatographed on a 1 ml Mono Q column. cGMP-selective PDE (PDE V) was obtained from porcine lung using chromatography on DEAE-cellulose and Mono Q columns; a calmodulin-affinity column was used to remove residual PDE I activity.

Characteristics of phosphodiesterase isoenzymes

With the exception of PDE II, which displayed positive cooperativity, all the preparations showed simple Michaelis-Menton kinetics (see Table 1 ).

PDE I The activity of this isoenzyme was stimulated by the $Ca^{2+}$-calmodulin complex. The isoenzyme could hydrolyse both cAMP and cGMP, the latter was the preferred substrate.

PDE II The activity of this isoenzyme with cAMP as a substrate was stimulated by cGMP. The isoenzyme could hydrolyse both cAMP and cGMP, the latter was the preferred substrate under basal conditions. The activity of this isoenzmye was unaffected by the $Ca^{2+}$-calmodulin complex.

PDE III The activity of this isoenzyme with cAMP as a substrate was inhibited by cGMP. The isoenzyme could hydrolyse both cAMP and cGMP, the former was the preferred substrate. The activity of this isoenzmye was unaffected by the Ca²⁺-calmodulin complex.

PDE IV This isoenzyme had high affinity for cAMP, the hydrolysis of which was not inhibited by cGMP. The activity of this isoenzmye was unaffected by the Ca2+-calmodulin complex.

PDEV This isoenzyme had high affinity for cGMP. The activity of this isoenzmye was unaffected by the Ca²⁺-calmodulin complex.

Assay of phosphodiesterase activity

PDE activity was assayed by the boronate column method as previously described (Reeves et al., 1987). The enzymes were assayed by incubation at 37° C. for 4–30 min in 50 mM Tris, 5 mM MgCl$_2$, pH 7.5 with ³H-labelled cyclic nucleotide (4×105 disintegrations min⁻¹) and ¹⁴C-labelled nucleotide 5'-monophosphate (3×10³ disintegrations min⁻¹). The assay was stopped by boiling, and the ³H-labelled 5'-monophosphate product separated from substrate on boronate columns. The reaction mixture was diluted with 0.5 mL 100 mM HEPES [N-(2-hydroxyethyl)piperazine-N ¹-2-ethanesulfonic acid], 100 mM NaCl, pH 8.5, and applied to the column. The column was extensively washed with the same buffer, and the 5'-nucleotide eluted with 6mL of 0.25M acetic acid. The recovery of product as judged by ¹⁴C-recovery was approximately 80%. All assays were linear with time of incubation and concentration of enzyme over the range used in these experiments. IC50 values (the concentration of inhibitor required for 50% inhibition of activity) were obtained by incubation of the isoenzyme using 1 mM cAMP as a substrate for PDE I (in the absence of Ca²⁺ and calmodulin), PDE II and PDE V and with 1 mM cAMP as a substrate for PDE III and PDE IV.

A range of inhibitor concentrations from 0.1×IC$_{50}$ to 100×IC$_{50}$ was used.

References

BEAVO, J. A. AND D. H. REIFSNYDER, Primary sequence of cyclic nucleotide phosphodiesterase isozymes and the design of selective inhibitors. Trends. Pharmacol. Sci. 11, 150–155 (1990).

REEVES M. L., B. K. LEIGH and P. J. ENGLAND, The identification of a new cyclic nucleotide phosphodiesterase activity in human and guinea-pig cardiac ventricle. Biochem. J. 241, 535–541 (1987).

TABLE 1

| Kinetic properties of phosphodiesterase isoenzymes | | | |
|---|---|---|---|
| | Km (μM) | | Vmax cGMP |
| Isoenzyme | cAMP | cGMP | Vmax cGMPI. |
| I. Ca²⁺/calmodulin-stimulated | 36 | 5 | 5 |
| II. cGMP-stimulated[a] | 45 | 14 | 1 |
| III. cGMP-inhibited | 0.5 | 0.1 | 5 |
| IV. cAMP-specific | 2 | > | n.d. |
| V. cGMP-specific | > | 1 | n.d |

[a]enzyme displayed positive cooperativity
> Km > 100 mM
n.d. not determined, due to inability of PDE to hydrolyse one of the substrates.

| Example No. | Inhibition of PDE expressed as IC$_{50}$ (mM) | |
|---|---|---|
| | PDE (IV) | PDE (V) |
| 1 | 3.0 | 4 |
| 2 | 3.0 | 0.4 |
| 3 | 4.0 | 0.2 |
| 7 | 11 | >100 |
| 9 | 4 | 0.9 |
| 19 | 3 | 0.4 |
| 23 | >100 | 7 |

-continued

| Example No. | Inhibition of PDE expressed as IC$_{50}$ (mM) | |
|---|---|---|
| | PDE (IV) | PDE (V) |
| 24 | 2 | 2 |
| 25 | >100 | 37 |

It is claimed:

1. A compound of formula (I):

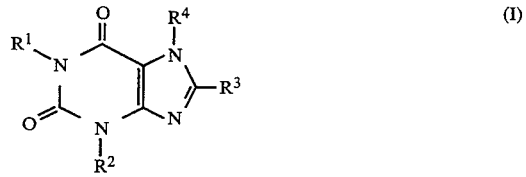

or, if appropriate, a pharmaceutically acceptable salt thereof, wherein $R^1$ and $R^2$ each independently are an alkyl group or a moiety of formula (a):

wherein m is zero or an integer 1, 2 or 3 and A is a substituted or unsubstituted cyclic hydrocarbon radical, providing that when one of $R^1$ and $R^2$ is methyl then the other is not methyl;

$R^3$ is hydrogen, $NO_2$ or a halogen atom, an alkoxy group or a group of formula $NR^sR^t$ wherein $R^s$ and $R^t$ each independently is hydrogen or alkyl or $R^s$ and $R^t$ together with the nitrogen to which they are attached form a phthalimido group or $R^3$ is a moiety of formula (b):

wherein $R^5$ is alkyl or a aryl group; and $R^6$ is hydrogen or a group $SO_2R^7$ wherein $R^7$ is alkyl or aryl; $R^4$ is $SO_2R^8$, wherein $R^8$ is alkyl or aryl, or, providing $R^3$ is a moiety of the above-defined formula (b), then $R^4$ may also represent hydrogen, alkyl or benzyl.

2. A method for the treatment and/or prophylaxis of disorders associated with allergic disorders associated with atopy in the human or animal body, which method comprises administering a non-toxic, pharmaceutically acceptable amount of a compound of formula (I) according to claim 1 or if a pharmaceutically acceptable salt thereof.

3. A compound according to claim 1 wherein A is a cyclopropyl group.

4. A compound according to claim 1 wherein $R^3$ is hydrogen, a halogen atom, a group of the formula $NR^sR^t$, or a moiety of the formula (b).

5. A compound according to claim 1 wherein $R^3$ is a group of formula $NR^sR^t$.

6. A compound according to claim 1 wherein $R^8$ is an aryl group.

7. A compound according to clam 1 wherein $R^8$ is phenyl,4-methoxyphenyl, 3,4-dimethoxyphenyl, 2,5-dimethoxyphenyl, (2-methoxy,5-bromo)phenyl and 4-nitrophenyl, 3- or 4-trifluoromethylphenyl, (3,5-di-trifluoromethyl)phenyl, 4-chlorophenyl,4-methylphenyl, 3,4,5-trimethoxyphenyl and 2-methoxycarbonylphenyl.

8. A compound according to claim 1 wherein R 8 is 4-methoxyphenyl.

9. A pharmaceutical composition comprising a compound of formula (I), according to claim 1 or a pharmaceutically acceptable salt thereof and a pharmaceutically acceptable carrier.

* * * * *